United States Patent
Kim et al.

(10) Patent No.: US 12,102,501 B2
(45) Date of Patent: Oct. 1, 2024

(54) SYMMETRICAL ADVANCEMENT OF MANDIBLE

(71) Applicant: PROSOMNUS SLEEP TECHNOLOGIES, INC., Pleasanton, CA (US)

(72) Inventors: Sung Kim, Pleasanton, CA (US); David W. Kuhns, Pleasanton, CA (US); Leonard A. Liptak, Pleasanton, CA (US)

(73) Assignee: PROSOMNUS SLEEP TECHNOLOGIES, INC., Pleasanton, CA (US)

( * ) Notice: Subject to any disclaimer, the term of this patent is extended or adjusted under 35 U.S.C. 154(b) by 634 days.

(21) Appl. No.: 17/051,143

(22) PCT Filed: Apr. 26, 2019

(86) PCT No.: PCT/US2019/029471
§ 371 (c)(1),
(2) Date: Oct. 27, 2020

(87) PCT Pub. No.: WO2019/210253
PCT Pub. Date: Oct. 31, 2019

(65) Prior Publication Data
US 2021/0228320 A1    Jul. 29, 2021

Related U.S. Application Data

(60) Provisional application No. 62/663,873, filed on Apr. 27, 2018.

(51) Int. Cl.
*A61C 7/08* (2006.01)
*A61F 5/56* (2006.01)

(52) U.S. Cl.
CPC ........... *A61C 7/08* (2013.01); *A61F 5/566* (2013.01)

(58) Field of Classification Search
CPC .... A61C 7/08; A61C 7/10; A61C 7/36; A61F 5/56; A61F 5/566; A61F 2005/563; A61F 2/2803
(Continued)

(56) References Cited

U.S. PATENT DOCUMENTS 6,604,527 B1 * 8/2003 Palmisano ............... A61C 7/08
                                                      128/859
9,808,327 B1   11/2017 Kim et al.
(Continued)

FOREIGN PATENT DOCUMENTS

WO   WO-2010087824 A1 *  8/2010 ............... A61C 7/08
WO      2017/149523 A1    9/2017

OTHER PUBLICATIONS

International Search Report and Written Opinion issued in PCT/US2019/029471 on Sep. 20, 2019 (13 pages).

*Primary Examiner* — Ophelia A Hawthorne
*Assistant Examiner* — Michael Milo
(74) *Attorney, Agent, or Firm* — Procopio, Cory, Hargreaves & Savitch LLP

(57) ABSTRACT

Disclosed are asymmetrical splints for a mandibular advancement device (MAD) for use with a patient having an asymmetrical dentition, wherein the asymmetry of the splint complements the asymmetry of the dentition such that when the MAD is used to advance the mandible, the mandible is advanced symmetrically. Also disclosed are methods of manufacture and use of the splints.

7 Claims, 2 Drawing Sheets

(58) Field of Classification Search
USPC .......................................................... 128/848
See application file for complete search history.

(56) References Cited

U.S. PATENT DOCUMENTS

| | | | | |
|---|---|---|---|---|
| 9,820,882 | B2 | 11/2017 | Liptak et al. | |
| 2009/0113714 | A1* | 5/2009 | Greenberg | B21F 43/00 |
| | | | | 29/896.11 |
| 2016/0184129 | A1* | 6/2016 | Liptak | A61C 7/08 |
| | | | | 128/848 |
| 2016/0199216 | A1* | 7/2016 | Cam | A61F 5/566 |
| | | | | 128/848 |
| 2016/0378883 | A1* | 12/2016 | Lucas | G06F 30/20 |
| | | | | 703/1 |
| 2017/0165042 | A1 | 6/2017 | Hillukka | |
| 2018/0024530 | A1 | 1/2018 | Kim et al. | |
| 2019/0015246 | A1 | 1/2019 | Kim et al. | |
| 2019/0105191 | A1 | 4/2019 | Sung et al. | |
| 2020/0163795 | A1* | 5/2020 | Garcia et al. | A61F 5/566 |

\* cited by examiner

SYMMETRICAL ADVANCEMENT OF MANDIBLE

CROSS-REFERENCE TO RELATED APPLICATIONS

The present invention is filed under 35 U.S.C. § 371 as the U.S. national phase of International Patent Application No. PCT/US2019/029471, filed 26 Apr. 2029 (26.04.2019), which designated the U.S. and claims the benefit of priority to U.S. Provisional Application No. 62/663,873, filed Apr. 27, 2018, each of which is incorporated herein by reference.

FIELD OF THE INVENTION

The present invention is in the field of mandibular advancement devices.

BACKGROUND OF THE DISCLOSURE

Mandibular advancement devices (MADs) have been used extensively to treat conditions such as sleep apnea. A fundamental problem with the currently marketed MADs is the adjustment of an asymmetrical jaw. Regardless of the adjustment mechanism used, whether jack screw, Herbst, microtitration, etc., the MAD is advanced symmetrically to make adjustments. For example, in a device with a jack screw advancement mechanism, both sides of the splint are advanced at exactly the same distance. However, given the asymmetry of the jaw, the symmetrical advancement will cause the mandible to advance asymmetrically, causing additional problems, such as pain in the temporal-mandibular joint (TMJ). Therefore, a need exists in the art to develop MADs that take the asymmetry of the jaw into account to advance the mandible symmetrically.

SUMMARY OF THE INVENTION

Disclosed are asymmetrical splints for a mandibular advancement device (MAD) for use with a patient having an asymmetrical dentition, wherein the asymmetry of the splint complements the asymmetry of the dentition such that when the MAD is used to advance the mandible, the mandible is advanced symmetrically. Also disclosed are methods of manufacture and use of the splints.

DETAILED DESCRIPTION OF THE EMBODIMENTS

Figure 1:
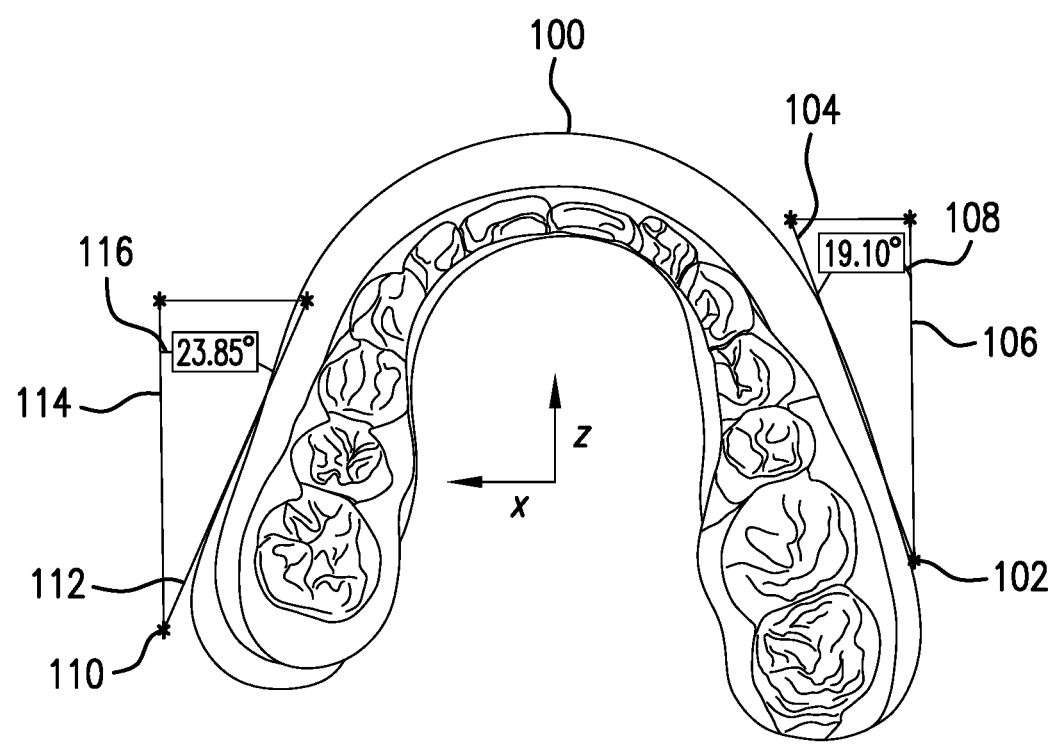
FIG. 1 is an illustration of an asymmetrical splint.

A concern among health care providers (HCPs) in using MADs is the concept of unwanted, asymmetrical, titration. Simply put, fifty turns of the expansion screw on the left side of the device usually does not express the same NP titration as fifty turns of the expansion screw on the right. This often results in extra adjustments, appointments, and an overall increased challenge of controlling the case.

There are two main sources of asymmetrical titration errors: anatomical variance and fabrication variance. Anatomical variance is the acknowledgement that arch forms are rarely symmetrical. Arch forms vary from patient to patient, from left side to right. These natural, anatomical, variances result in different A/P titration when an expansion screw is adjusted. For example, if the right side of the arch presents a 29-degree angle, 6.0 mm of expansion screw displacement will express 5.3 mm of A/P advancement. However, if the left side of the arch presents a 14-degree angle, 6.0 mm of expansion screw displacement will express 5.8 mm of A/P advancement, a 0.5 mm difference between the left and right. Limitations of the traditional, artisanal fabrication method for OAT devices is the second source of asymmetrical titration errors. It is challenging for a technician to embed each expansion screw in perfect symmetry with respect to the A/P titration path, particularly when the anatomy itself is likely not perfectly symmetrical. Expansion screw assembly errors in the X, Y and Z dimensions result in three-dimensional errors that make it challenging to achieve the target NP location.

It has also been found that existing continuous advancement OAT devices are prone to breakage in the expansion screw assembly region. The titration mechanisms of existing continuous advancement OAT devices are ostensibly lever arms. Cantilever forces generated during routine OAT usage are amplified by the traditional lever arm design. The stress from the normal intraoral forces associated with OAT are concentrated toward the distal regions of the titration mechanisms.

As a result, traditional continuous advancement OAT devices can break more frequently than is desirable. Breakage often results in a series of clinical and therapeutic inefficiencies, not to mention the potential for the patient being out of treatment until a device is repaired or replaced.

Disclosed herein are mandibular advancement devices (MADs) that are designed and manufactured asymmetrically to match the asymmetry of the patient's dentition. They asymmetry of the MAD causes the position of the mandible as a whole to be adjusted symmetrically when the MAD is adjusted to advance the mandible.

Various aspects of the splints disclosed herein have already been made public. For example, the microtitration mechanism and the use of fins in affecting the proper titration is disclosed in U.S. Pat. No. 9,820,882 by Liptak et al. (Ser. No. 14/809,208). The computer aided design of the splints disclosed herein is described in US Patent Application Publication US2018/0024530A1 by Kim et al. (Ser. No. 15/651,874). The automated method of manufacturing the splints disclosed herein is described in U.S. Pat. No. 9,808,327 by Kim et al. (Ser. No. 15/416,715). MADs having a guide channel for the advancement mechanism is described in US Patent Application Publication US2019/0015246A1. Fin sleeves are disclosed in US Patent Application Publication US 20190105191A1. All of the aforementioned publications are hereby incorporated herein by reference in their entirety, including the drawings.

Thus, in one aspect disclosed here in are asymmetrical splints for a mandibular advancement device (MAD) for use with a patient having an asymmetrical dentition, wherein the asymmetry of the splint complements the asymmetry of the dentition such that when the MAD is used to advance the mandible, the mandible is advanced symmetrically.

Throughout the present disclosure, "dentition" refers to the entire anatomy of a person that relates to the teeth. Accordingly, "dentition" comprises all teeth, the mandible, and the maxilla.

In some embodiments, the asymmetry in the dentition is due to asymmetry in mandible, maxilla, or both.

To eliminate the need to count, record and communicate turns of the expansion screw during adjustments and to compensate for the aforementioned A/P titration asymmetries, fiducial markings are scored into the occlusal surface of the splint. new fiducial markings feature corresponds to the true A/P titration, and not how far the screw has been adjusted. The disclosed devices are manufactured by automatically calculating the trigonometry for each fiducial marking to compensate for the curvature of each side of each arch. In other words, a +1.0 mm adjustment according to the fiducial marks relates to +1 mm of true, anterior/posterior titration. In certain embodiments, the asymmetry in the splint is mathematically calculated based on the data obtained regarding the asymmetry of the dentition.

The inventive concepts disclosed here are now described in view of the non-limiting illustrative embodiments. The discussion that follows relates to the mathematical design of the splint. Accordingly, all references are to the computer aided design (CAD) representation of a splint, and not to a physical splint.

FIG. 1 shows a splint 100 that was designed for an asymmetrical dentition. The z axis is parallel the anteroposterior (A/P) axis, which intersects the back of the throat and the front incisors. The x axis is parallel to the dextro-sinister (DS) axis, which goes through the cheeks. When advancing a mandible, the desire is for the advancement to be along the z axis only.

A point 102 and a point 110 are selected on the right side and the left side of the splint, respectively. The adjustment mechanism, such as a fin, a Herbst device, a jack screw, etc., would be attached to the splint at this point. Tangent lines 104 & 112 to the splint curvature at points 102 and 110, respectively, are drawn. Further, lines 106 & 114 are drawn parallel to the z axis intersecting at points 102 & 110, respectively. Tangent angle 108 on the right side and tangent angle 116 on the left side between the tangent line 104,112 and the parallel line 106,114 are determined. In the particular embodiment shown in FIG. 1, tangent angle 108 is 19.10° and tangent angle 116 is 23.85°.

The tangent lines 104 & 112 represent the direction of advancement of the mandible by an advancement mechanism, such as a jack screw. As can be seen, the advancement is in a direction that rests at an angle away from a pure advancement along the A/P axis. Because the tangent angles on the two sides of the splint are not identical, if the advancement mechanism is caused to make a certain advancement on both sides of the splint, the advancement along the A/P axis would be unequal on either side.

The inequality between the advancement along the A/P axis can be calculated trigonometrically as follows:

cos tangent angle=parallel line/tangent line parallel line=tangent line×cos tangent angle In the example shown in FIG. 1, then, if the MAD is caused to advance 5 mm, the actual advancement of the mandible would be as follows:
Right Side:

parallel line=tangent line×cos tangent angle parallel line=5 mm×cos 19.10°=5 mm×0.95 parallel line=4.7 mm

Left Side:

parallel line=tangent line×cos tangent angle parallel line=5 mm×cos 23.85°=5 mm×0.9 parallel line=4.6 mm

Therefore, when a splint is caused to advance symmetrically, i.e., to the same extent on both sides of the splint, the actual advancement of the splint, and thus the mandible, is reduced by a multiple, which multiple is the cosine of the tangent angle between the parallel and tangent lines. Because the tangent angles on the two sides of the splint are not the same, the splint, and thus the mandible, advances asymmetrically along the z axis. The asymmetrical advancement causes stress on the mandible, the maxilla, and the temporomandibular joint (TMJ), which can cause increased discomfort, headaches, joint pain, or joint misalignment.

The present inventors have determined that if the process of calculating the extent of advancement described above is reversed, one can advance the mandible symmetrically by asymmetrically advancing the MAD. We now refer back to the example of FIG. 1 to exemplify this process. If the desire is to advance the mandible by 5 mm, then the following calculations are appropriate:
Right Side:

tangent line=parallel line÷cos tangent angle tangent line=5 mm÷cos 19.10°=5 mm÷0.95 tangent line=5.3 mm

Left Side:

tangent line=parallel line÷cos a tangent angle tangent line=5 mm÷cos 23.85°=5 mm÷0.91 tangent line=5.5 mm

Therefore, if one were to advance the right side of the splint by 5.3 mm and the left side by 5.5 mm, then one would obtain a mandibular advancement of 5 mm along the A/P, or z, axis. This symmetrical advancement of 5 mm on both sides reduces, and perhaps eliminates, any complications due to the asymmetry in the jaw and results in a much more comfortable and efficacious mandibular advancement device.

In some embodiments, the splints disclosed herein comprise fiducial marks 300 on the splint indicating the extent of mandibular protrusion subsequent to an adjustment to the MAD. In certain embodiments, the fiducial marks 300 are calculated to indicate the extent of a symmetrical mandibular advancement in the anterior-posterior direction. Therefore, a 1 mm fiducial mark does not indicate an advancement of 1 mm along the tangent line, which is what the currently marketed devices provide. Instead, the 1 mm fiducial mark represents a 1 mm advancement along the A/P axis. therefore, the fiducial markings 300 of the splints disclosed herein take into account the angular discrepancy on either side of the splint such that the fiducial markings 300 represent actual advancement along the A/P axis.

In some embodiments, the placement of the fiducial markings 300 is independent of the titration mechanism used. Thus, the conversion scheme described herein can be used with any available titration mechanism, or any titration mechanism developed in the future. In some embodiments, the titration mechanism is selected from control screw type, such as jack screw; mechanical hinge, such as a Herbst device; strap; a post or fin; microtitration mechanism, and the like.

In some embodiments, an accessory is mathematically calculated to be placed in a precise location to account for the dentition asymmetry such that the use of the accessory contributes to, or does not interfere with, the symmetrical advancement of the mandible. Of course, the location of the accessory is dependent on the function of the accessory. For instance, if the accessory is a fin or a mechanical hinge that is directly involved in the advancement mechanism, then the accessory is placed at points 102,110. However, other accessories, such as a ball clasp retention mechanism, a sensor, and the like, can be placed in other locations on the splint such that their placement does not interfere with the calculated tangent angles 108,116.

In some embodiments, the accessory is selected from a ball clasp, retention wire, treatment wire, alignment wires, a tongue behavior modification wire, post-manufacturing attachable fin, affixed fin sleeve, removable fin sleeve, metallic ball clasps, plastic ball clasps, dental buttons, soft liner, a compliance chip, an electronic or microelectronic device, a "smart" accessory (i.e., an electronic device that obtains data and communicates the data with another electronic device), strap, anterior hinge, or any other appliance accessory now known or designed in the future. In some embodiments, the accessory is selected from a pre-designed library of like accessories.

In some embodiments, a series of splints having the identical basic arch design are prepared. The aforementioned and already-incorporated '882 patent discloses one situation where design of such a series is desired, for example for a microtitration series having splints with fins located at a different distance from the back of the splint. The asymmetrical design disclosed herein is such that an accessory, for example a fin, can be placed in one location for one splint in the series and another location for another splint in the series, without the need to change the tangent angle or make any other modifications to accommodate both the asymmetry and the accessory. Therefore, the asymmetrical design of the splint allows for an accessory to be relocated from one location on the splint to a second location without altering the trigonometric calculations discussed above.

Figure 2:
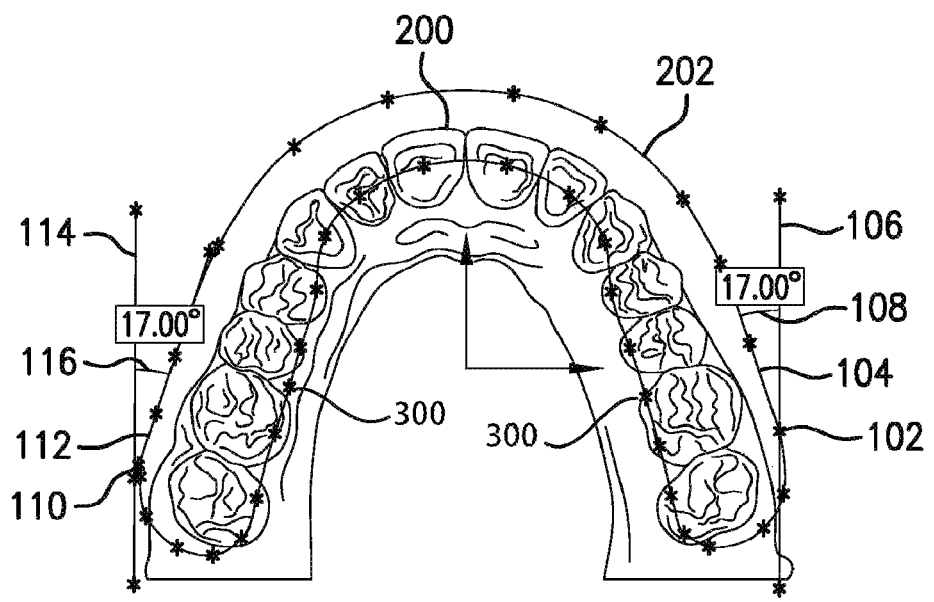
FIG. 2 is an illustration of the design of a symmetrical splint for an asymmetrical dentition.

FIG. 2 illustrates another aspect of the asymmetrical design disclosed herein. In the embodiments within this aspect, the splint is designed such that the tangent and parallel lines make the same tangent angle on both sides of the splint. The dentition 200 is surrounded by the mathematical design of the outline 202 of the splint. The splint outline 202 is prepared such that the tangent angle on both sides is exactly the same. In the illustrative example of FIG. 2, this tangent angle 108,116 is set to be 17.00° on both sides.

The two different methodologies, i.e., calculating the fiducial marks 300 based on the tangent angles or designing the tangent angles to be identical, each provide advantages and disadvantages of their own. In the first aspect, as illustrated by FIG. 1 and the relevant discussion above, the splint is designed as less bulky as possible to provide maximum patient comfort. However, computed fiducial markings 300 are necessary to affect a proper symmetrical advancement. In the second aspect, as illustrated by FIG. 2, the advancement is always symmetrical, though the actual advancement needs to be calculated. However, the fiducial markings 300 on both sides are identical. A disadvantage of this method is that the splint is bulkier on one side than the other in order to provide the proper tangent line 104,112 to create the same tangent angles 108,116 on both sides. A bulkier splint, or an asymmetrically bulky splint can cause additional patient discomfort.

The choice of the mechanism used for the design of the splint is dictated by the patient anatomy, the patient's specific medical needs, and the health care provider or the patient's personal preference.

In some embodiments, the HCP is a dentist. In other embodiments, the HCP is a dental technician. In other embodiments, the HCP is a sleep disorder specialist. In certain embodiments, the HCP is an individual charged with altering the position of the patient's mandible (e.g., the use of mandibular advancement devices). In other embodiments, the HCP is an individual charged with straightening a patient's teeth (orthodontia) (e.g., the use of braces and the like). In other embodiments, the HCP is a Temporal Mandibular Joint (TMJ) and Disease (TMD) specialist who repositions the mandible to manage pain. In certain embodiments, the patient is a human.

In another aspect, disclosed herein is a method of design and manufacture of an MAD, or a splint for an MAD, as described herein. The basic design and manufacture process is fully disclosed in, for example, the above-incorporated U.S. Pat. No. 9,808,327, inter alia at column 3, lines 20-31 and the relevant subsequent discussion. In addition to the basic design process, the process for the design and manufacture of the splints disclosed herein require the introduction of the tangent angle and the advancement conversion as discussed herein.

In another aspect, disclosed herein is a method of treating or ameliorating a jaw-related disorder, sleep apnea, teeth grinding, or improperly positioned mandible in a patient by obtaining a dental device manufactured by the methods disclosed above and positioning the dental device over the dentition prior to sleep. The device then advances the mandible forward relative to the maxilla, thereby ameliorating the symptoms of sleep apnea or the jaw-related disorder. In some embodiments, the method further comprises instructing the patient in the use of the device. In some embodiments, the jaw-related disorder is selected from temporomandibular disorder (TBD), poorly positioned temporomandibular joint (TMJ), or aesthetic deficiencies.

What is claimed is:

1. An asymmetrical splint for a mandibular advancement device (MAD) for use with a patient having an asymmetrical dentition, wherein the asymmetry of the asymmetrical splint complements the asymmetry of the dentition such that when the mandibular advancement device (MAD) is used to advance the mandible the mandible is advanced symmetrically, wherein the asymmetrical splint comprises an occlusal surface and fiducial markings scored into the occlusal surface, and wherein the fiducial markings compensate for the curvature of each side of each arch by being placed on the occlusal surface in a location mathematically calculated to account for a patient's asymmetrical dentition such that the fiducial markings mark an extent of a symmetrical advancement of the mandible by the mandibular advancement device (MAD) of the asymmetrical dentition, wherein asymmetrical advancement for each of a right and left side of the asymmetrical splint is determined by: tangent line=parallel line÷cos (tangent angle) where, the tangent line is tangential to splint curvature at a point, the point is selected on the asymmetrical splint to which an adjustment mechanism of the mandibular advancement device (MAD) is to be attached, the parallel line is parallel to anteroposterior (A/P) axis, and the tangent angle is between the tangent line and the parallel line.

2. The asymmetrical splint of claim 1, further comprising fiducial markings on the splint indicating the extent of mandibular protrusion subsequent to an adjustment to the mandibular advancement device (MAD).

3. The asymmetrical splint of claim 2, wherein the fiducial markings are calculated to indicate the extent of a symmetrical mandibular advancement in an anterior-posterior direction.

4. The asymmetrical splint of claim 1, wherein the asymmetry in the dentition is due to asymmetry in the mandible, maxilla, or both.

5. The asymmetrical splint of claim 1, wherein the asymmetry in the splint is mathematically calculated based on data obtained regarding the asymmetry of the dentition and Equation (1).

6. The asymmetrical splint of claim 1, wherein the mandibular advancement device (MAD) is configured to advance the mandible symmetrically based on the asymmetry of the dentition by titrating based on the asymmetry of the asymmetrical splint complementing the asymmetry of the dentition.

7. The asymmetrical splint of claim 1, wherein the placement of the fiducial markings is independent of a titration mechanism used with the mandibular advancement device (MAD).

\* \* \* \* \*